United States Patent [19]

Kiyoto et al.

[11] Patent Number: 4,578,271

[45] Date of Patent: Mar. 25, 1986

[54] BIOLOGICALLY ACTIVE WS 6049 SUBSTANCES, A PROCESS FOR THE PRODUCTION THEREOF AND THEIR PHARMACEUTICAL COMPOSITIONS

[75] Inventors: Sumio Kiyoto, Urawa; Motoaki Nishikawa, Toyonaka; Morita Iwami, Takarazuka; Hiroshi Terano, Toyonaka; Masanobu Kohsaka, Sakai, all of Japan

[73] Assignee: Fujisawa Pharmaceutical Co., Ltd., Osaka, Japan

[21] Appl. No.: 491,170

[22] Filed: May 3, 1983

[30] Foreign Application Priority Data

May 24, 1982 [GB] United Kingdom ............... 8215123

[51] Int. Cl.$^4$ ................. A61K 35/00; C12P 13/00; C12P 1/06; C12R 1/03
[52] U.S. Cl. ................................. 424/117; 435/128; 435/169; 435/825
[58] Field of Search ............... 435/128, 253, 825, 169, 435/170, 171; 424/115, 117, 118

[56] References Cited

U.S. PATENT DOCUMENTS 4,195,079 3/1980 Celmer et al. ................... 424/122

FOREIGN PATENT DOCUMENTS 2069500 8/1981 United Kingdom .

OTHER PUBLICATIONS

Ohkuma, H. et al., *J. of Antibiotics*, vol. 33, No. 10, pp. 1087–1097, 1980.
Tomita, K. et al., J. of Antibiotics, vol. 33, No. 10, pp. 1098–1102, 1980.
European Search Report for European Patent Application No. 83104988.

*Primary Examiner*—Alvin E. Tanenholtz
*Assistant Examiner*—Jayme A. Huleatt
*Attorney, Agent, or Firm*—Oblon, Fisher, Spivak, McClelland & Maier

[57] ABSTRACT

Novel compounds designated as WS 6049-A and WS 6049-B are disclosed, as well as compositions containing the compounds thereof, a method of treating microbial infections, a method of prolonging the survival time of the patient with lymphocytic leukemia by administering the compounds thereof, and a process for making the WS 6049 substances, are disclosed. As indicated above, the novel compounds have antimicrobial and antileukemic activities which make them useful against a variety of pathogenic microorganisms and leukemic tumors.

8 Claims, 4 Drawing Figures

Figure 1:
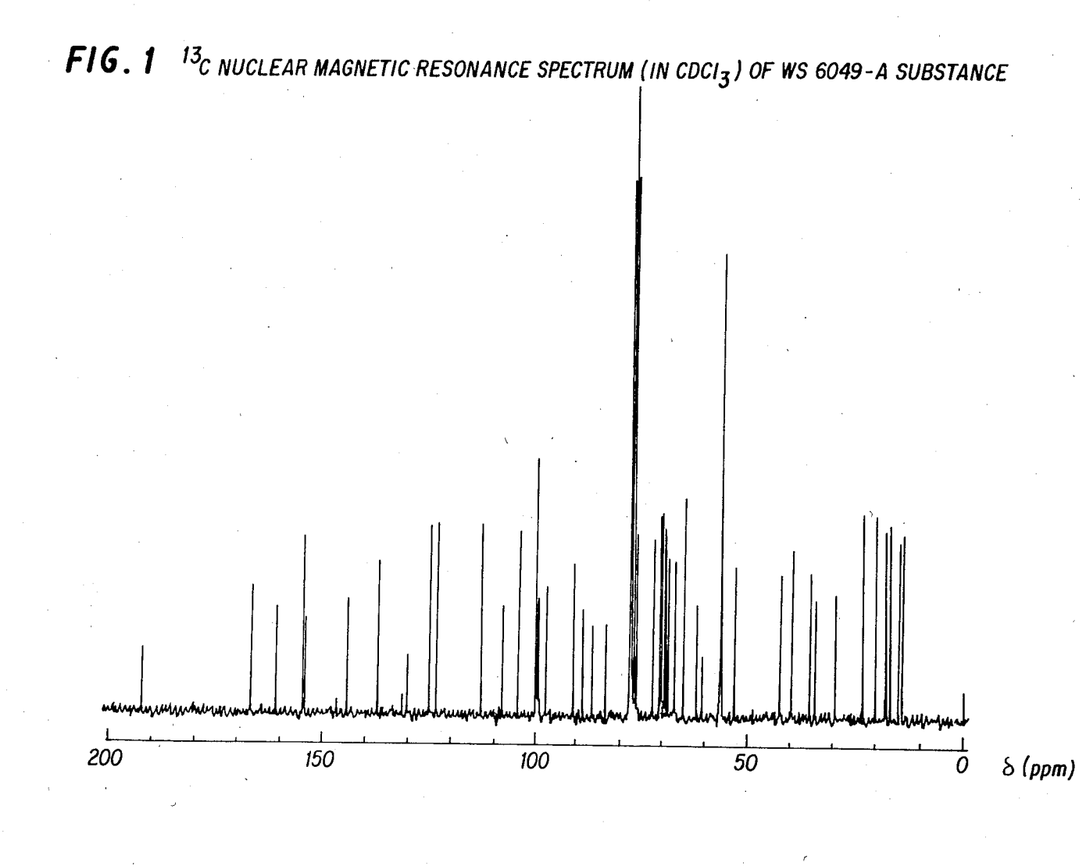

FIG. 1 13C NUCLEAR MAGNETIC RESONANCE SPECTRUM (IN CDCl3) OF WS 6049-A SUBSTANCE

Figure 2:
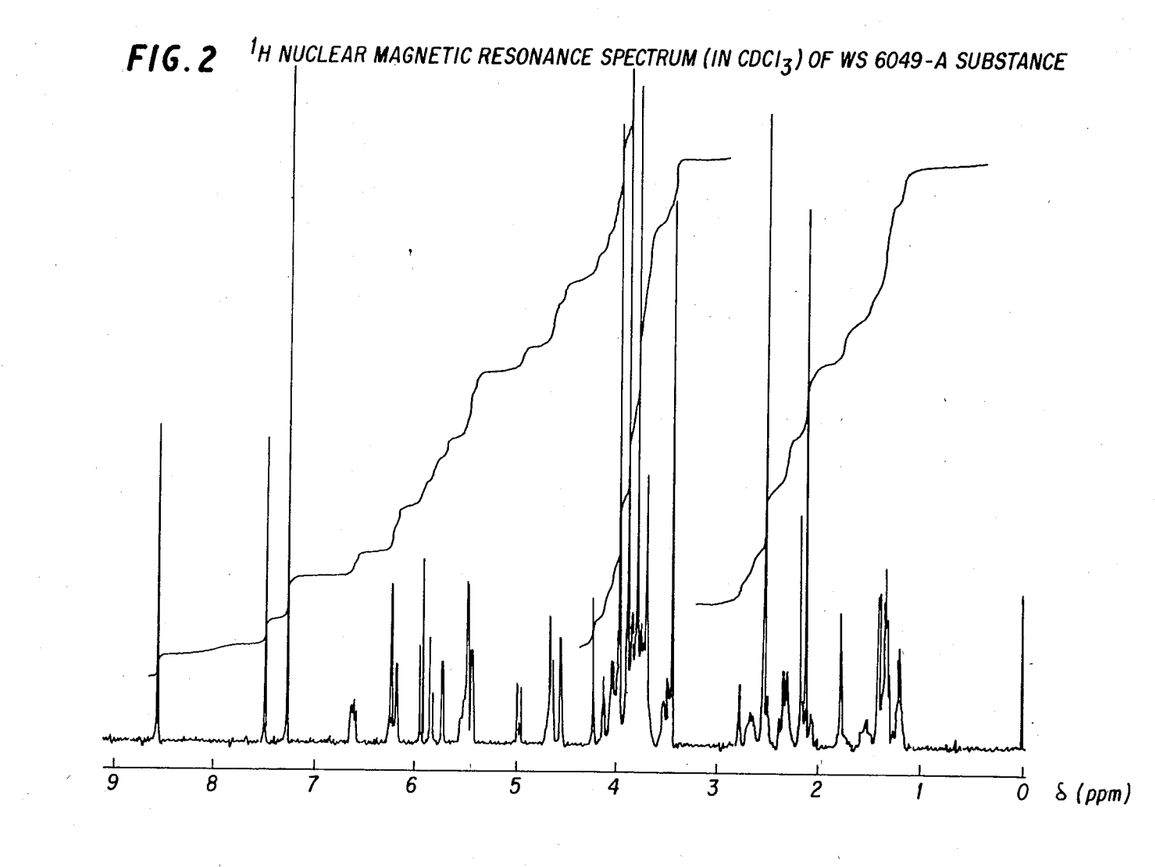

FIG. 2  $^1$H NUCLEAR MAGNETIC RESONANCE SPECTRUM (IN $CDCl_3$) OF WS 6049-A SUBSTANCE

Figure 3:
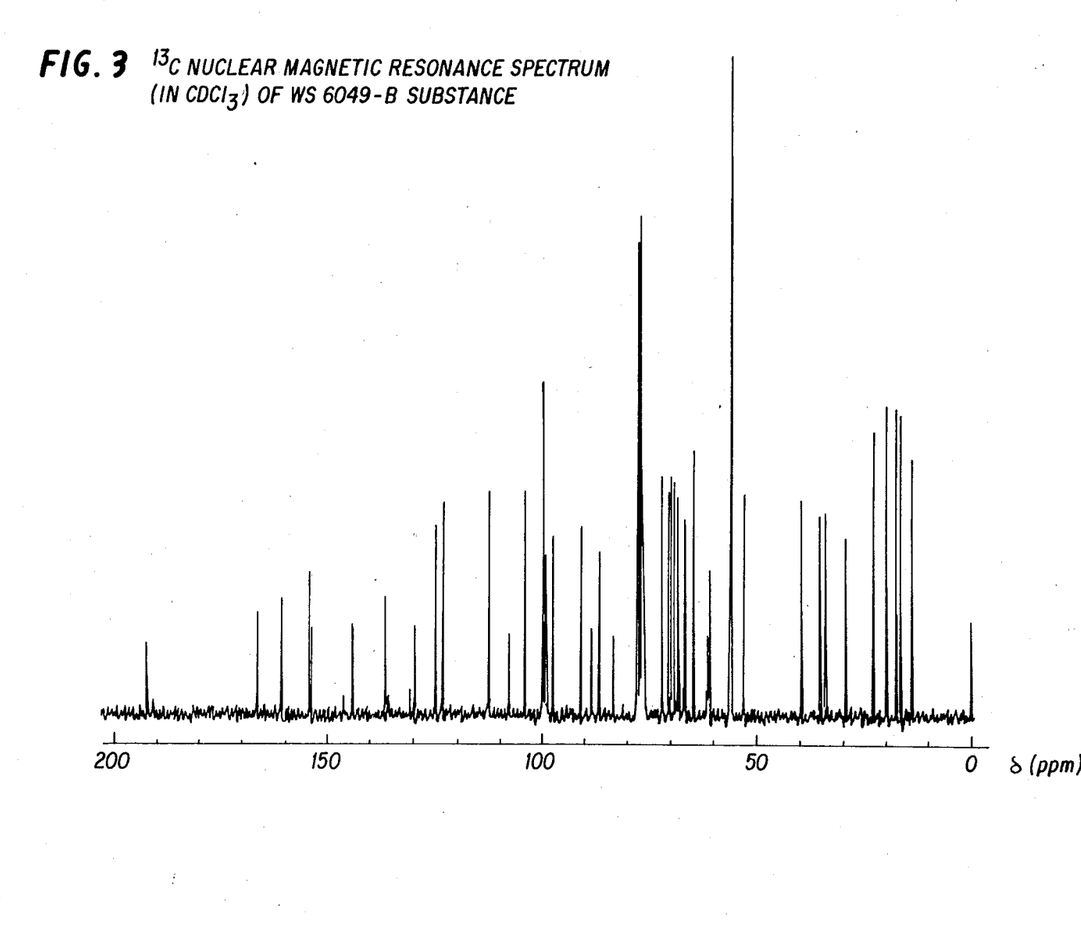

FIG. 3  $^{13}C$ NUCLEAR MAGNETIC RESONANCE SPECTRUM (IN $CDCl_3$) OF WS 6049-B SUBSTANCE

Figure 4:
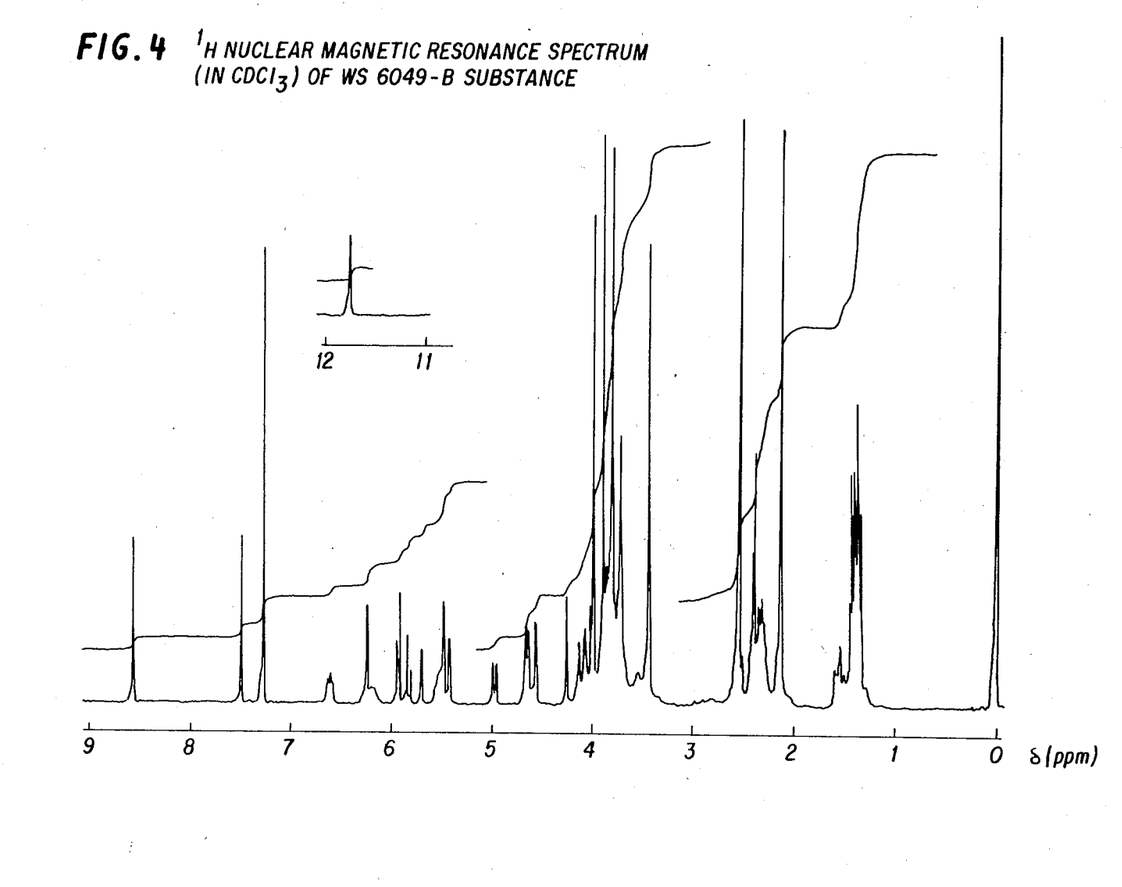

FIG. 4  $^1H$ NUCLEAR MAGNETIC RESONANCE SPECTRUM (IN $CDCl_3$) OF WS 6049-B SUBSTANCE

BIOLOGICALLY ACTIVE WS 6049 SUBSTANCES, A PROCESS FOR THE PRODUCTION THEREOF AND THEIR PHARMACEUTICAL COMPOSITIONS

BACKGROUND OF THE INVENTION

Field of the Invention

This invention relates to new compounds having biological activities, hereinafter referred to as WS 6049 substances. More particularly, this invention relates to a new biologically active WS 6049-A substance and WS 6049-B substance, which have antimicrobial activities against various pathogenic microorganism and antitumor activities, to a process for the preparation thereof and to pharmaceutical compositions containing the same.

SUMMARY OF THE INVENTION

This invention provides new WS 6049 substances which are active against various pathogenic microorganisms and tumors, and useful for the therapeutical treatment of infectious diseases and of tumors in mice.

This invention provides a process for the production of WS 6049 substances by fermentation.

This invention provides a pharmaceutical compositions containing, as an active ingredient, WS 6049 substances, Description of the Prior Art In the preceding and following descriptions, it is to be noted that the wording "WS 6049 substances" is intended to include WS 6049-A substance and WS 6049-B substance.

WS 6049 substances of this invention can be produced by fermentation of WS 6049 substance-producing strain belonging to the genus Actinomadura such as *Actinomadura pulveraceus* sp. nov. No. 6049 or the like in a nutrient medium.

Particulars of the microorganism used for producing the WS 6049 substances and the method of production thereof will be explained in the following paragraphs.

THE MICROORGANISM

The microorganism which can be used for the production of WS 6049 substances is a strain belonging to the genus Actinomadura, among which a strain of *Actinomadura pulveraceus* sp. nov. No. 6049 has been newly isolated from a soil sample collected at Wakayama City in Wakayama Prefecture, Japan.

A culture of the newly isolated living organism of *Actinomadura pulveraceus* sp. nov. No. 6049 has been deposited with and added to a stock culture collection of the American Type Culture Collection under the Budapest Treaty and its deposit number is ATCC 39100 (deposit date: Apr. 12, 1982).

It is to be understood that, for the production of WS 6049 substances, this invention is not limited to the use of the particular organism as described herein, which is given for illustrative purpose only.

Further, this invention also includes the use of any mutants which are capable of producing WS 6049 substances, including natural mutants which are produced by natural mutation of the organisms as well as artificial mutants which can be produced from the described organism by conventional means, such as X-rays, ultraviolet radiation, nitrogen mustard oils, etc. and genetic engineering means.

*Actinomadura pulveraceus* sp. nov. No. 6049 has the following morphological, cultural and physiological characteristics.

(1) Morphological characteristics:

The methods described by Shirling and Gottlieb were employed for observation of the morphological characteristics (Shirling, E. B. and D. Gottlieb: Methods for characterization of Streptomyces species, Int. J. Syst. Bacteriol. 16: 313–340, 1966).

Morphological observations were made with light and electron microscopy on cultures grown at 30° C. for 21 days on yeast extract-malt extract agar, inorganic salts-starch agar and oatmeal agar. The mature spores occurred in chains of 5 to 20 spores forming mainly hook and sometimes loose spirals. The spores were oval and $0.8-1.0 \times 1.2-1.4\mu$ in size with warty surfaces.

(2) Culturing characteristics:

Culturing characteristics were observed on ten kinds of media described by Shirling and Gottlieb (mentioned hereinabove) and Waksman (Waksman, S. A.: The Actinomycetes. Vol. 2. Classification, identification and description of genera and species. The Williams and Wilkins Co., Baltimore, 1961). The incubation was made at 30° C. for 21 days. The color names used in this study were based on Color Standard (Nihon Shikisai Co., Ltd.). As shown in Table 1, colonies belonged to the blue color series when the strain was grown on yeast extract-malt extract agar, oatmeal agar and inorganic salts-starch agar. Soluble pigment was not produced.

The cell-wall composition analysis was performed by the methods of Becker et al. (Becker, B., M. P. Lechevalier, R. E. Gordon and H. A. Lechevalier: Rapid differentiation between Nocardia and Streptomyces by paper chromatography of whole-cell hydrolysates, Appl. Microbiol. 12, 421–423, 1964) and Yamaguchi (Yamaguchi, T.: Comparison of the cell-wall composition of morphologically distinct actinomycetes, J. Bacteriol. 89, 444–453, 1965). The cell wall of this strain No. 6049 contained meso-diaminopimelic acid. A whole cell hydrolysate showed the presence of glucose, mannose and madurose (3-O-methyl-D-galactose).

(3) Biological and physiological properties:

Temperature range for growth and optimum temperature were determined on yeast extract-malt extract agar using temperature gradient incubator (Toyo Kagaku Sangyo Co., Ltd.). The pH range for growth and the optimum pH were determined by liquid cultivation in yeast extract-malt extract broth with shaking at 30° C. for 7 days. Gelatin liquefaction was examined at 30° C. for 14 days on gelatin medium. Starch hydrolysis was observed by the starch-iodine reaction after incubation on inorganic salts-starch agar plate at 30° C. for 14 days. Milk peptonization was observed in skim-milk medium at 30° C. for 14 days. Melanoid pigment production was observed on tyrosine agar, peptone-yeast extract-iron agar and tryptone-yeast extract broth. As shown in Table 2, temperature range for growth was from 20° C. to 41° C. with optimum from 30° C. to 35° C. Starch hydrolysis, milk peptonization, $H_2S$ production, urease activity, nitrate reduction and melanine production were negative, whereas gelatin liquefaction and milk coagulation were positive.

Utilization of carbon sources was examined according to the method of Pridham and Gottlieb (Pridham, T. G. and D. Gottlieb: The utilization of carbon compounds by some Actinomycetales as an aid for species determination, J. Bacteriol. 56:107–114, 1965). The results determined after 14 days incubation at 30° C. As shown in Table 3, almost all carbon sources were doubtfully or not utilized. Only D-xylose, D-glucose and D-trehalose were utilized. The aforementioned cell wall composition and whole cell sugar components indicate the strain No. 6049 is a species of the genus Actinomadura.

A comparison of this organism was made with the published descriptions of Actinomadura species (Nonomura, H. and Y. Ohara: Distribution of actinomycetes in soil, XI) Some new species of the genus Actinomadura Lechevalier et al., J. Ferment. Technol. 49:904–912, 1971; Goodfellow, M., G. Alderson and J. Lacey: Numerical taxonomy of Actinomadura and related actinomycetes, J. Gen. Microbiol. 112: 95–111, 1979; Tomita, K., Y. Hoshino, T. Sasahira and H. Kawaguchi: BBM-928, a new antitumor antibiotic complex 2. Taxonomic studies on the producing organism, J. Antibiotics 33: 1098–1102, 1980).

Strain No. 6049 is considered to resemble *Actinomadura verrucosospora*. It was found however, that strain No. 6049 could be differentiated from this species in the following points. As shown in Table 4, utilization of D-fructose, L-arabinose, mannitol, sucrose and glycerin is different. Differences are also observed in nitrate reduction and milk peptonization. Aerial mass color of strain No. 6049 belonged to the white color series on inorganic salts-starch agar, whereas that of *A. verrucosospora* belonged to the gray color series. Direct comparison of cultural characteristics between strain No. 6049 and *A. verrucosospora* was shown in Table 5.

As a result of above comparisons, strain No. 6049 is considered a new species of the genus Actinomadura. The name *Actinomadura pulveraceus* sp. nov. is proposed for strain No. 6049 referring to the powdery aerial mycelium on yeast extract-malt extract agar, oatmeal agar and inorganic salts-starch agar.

TABLE 1

Culturing characteristics of strain No. 6049

| Medium | Aerial Mycelium | Reverse Side Color | Soluble Pigment |
|---|---|---|---|
| Oatmeal agar | greenish white | colorless | none |
| Yeast extract-malt extract agar | pale blue | pale yellow | none |
| Inorganic salts-starch agar | white | light red | none |
| Glucose asparagine agar | none | pink | none |
| Glycerin-asparagine agar | trace | pale pink | none |
| Sucrose-nitrate agar | none | pale pink | none |
| Nutrient agar | none | light red | none |
| Potato-dextrose agar | none | pale pink | none |
| Tyrosine agar | grayish white | pale pink | none |
| Peptone-yeast extract-iron agar | none | pale pink | none |

TABLE 2

Physiological Properties of Strain No. 6049

| Temperature range for growth | 20° C.–41° C. |
|---|---|
| Optimum temperature | 30° C.–35° C. |
| pH Range for growth | 6–10 |
| Optimum pH | 7–8 |
| Nitrate reduction | negative |
| Starch hydrolysis | positive |
| Milk coagulation | weakly positive |
| Milk peptonization | negative |
| Gelatin liquefaction | positive |

TABLE 2-continued

Physiological Properties of Strain No. 6049

| Melanine production | negative |
|---|---|
| H$_2$S production | negative |
| Urease | negative |

TABLE 3

Carbon sources utilization of strain No. 6049

| C—sources | |
|---|---|
| none | — |
| Glycerin | ± |
| D-Xylose | + |
| Sodium citrate | — |
| Lactose | — |
| D-Fructose | — |
| Rhamnose | + |
| Maltose | ± |
| Sodium succinate | — |
| Inulin | — |
| Inositol | ± |
| Raffinose | — |
| D-Galactose | ± |
| L-Arabinose | — |
| D-Glucose | + |
| Mannitol | — |
| D-Mannose | — |
| Sucrose | + |
| Cellulose | — |
| D-Trehalose | — |
| Salicin | — |
| Chitin | — |
| Sodium acetate | — |

+: utilization
±: doubtful utilization
—: not utilization

TABLE 4

Different points of carbon utilization and physiological properties between strain No. 6049 and *Actinomadura verrucosospora*

| | No. 6049 | *A. verrucosospora* |
|---|---|---|
| D-Fructose | — | + |
| L-Arabinose | — | + |
| Mannitol | — | + |
| Sucrose | ++ | ± |
| Glycerin | ± | ++ |
| Nitrate reduction | negative | positive |
| Milk peptonization | negative | positive |

++: good utilization
+: utilization
±: doubtful utilization
—: not utilization

TABLE 5

Direct comparison between strain No. 6049 and *Actinomadura verrucosospora*

| Medium | Growth | Aerial Mycelium | Reverse Side Color | Soluble Pigment |
|---|---|---|---|---|
| | | Strain No. 6049 | | |
| 1 | abundant | none | pale yellow | none |
| 2 | poor | none | colorless | none |
| 3 | abundant | blue | pink | none |
| 4 | abundant | white | pink | none |
| 5 | moderate | grayish white | colorless | none |
| 6 | abundant | none | colorless | none |
| 7 | poor | grayish white | colorless | none |
| 8 | moderate | pale blue | pale pink | none |
| 9 | abundant | pinkish grey | pink | none |
| | | *Actinomadura verrucosospora* | | |
| 1 | moderate | none | pink | none |
| 2 | moderate | none | pink | none |
| 3 | poor | none | pink | none |
| 4 | poor | none | pale pink | none |
| 5 | moderate | grayish white | pink | none |

TABLE 5-continued

Direct comparison between strain No. 6049 and *Actinomadura verrucosospora*

| Medium | Growth | Aerial Mycelium | Reverse Side Color | Soluble Pigment |
|---|---|---|---|---|
| 6 | abundant | none | pink | none |
| 7 | poor | grayish blue | pink | none |
| 8 | abundant | pale bluish pink | pink | none |
| 9 | abundant | pale bluish pink | pink | none |

1: Peptone-yeast extract-iron agar,
2: Nutrient agar,
3: Potato-dextrose agar,
4: Sucrose-nitrate agar,
5: Tyrosine agar,
6: Yeast extract-malt extract agar,
7: Oatmeal agar,
8: Inorganic salts-starch agar,
9: Glucose-asparagine agar

PRODUCTION OF WS 6049 SUBSTANCES

The WS 6049 substances of this invention are produced when a WS 6049 substance-producing strain belonging to the genus Actinomadura (e.g. *Actinomadura pulveraceus* sp. nov. No. 6049) is grown in a nutrient medium containing sources of assimilable carbon and nitrogen under aerobic conditions (e.g. shaking culture, submerged culture, etc.).

The preferred sources of carbon in the nutrient medium are carbohydrates such as xylose, glucose, sucrose, starch and the like.

The preferred sources of nitrogen are yeast extract, peptone, gluten meal, cotton seed flour, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea, amino acid and the like.

The carbon and nitrogen sources, though advantageously employed in combination, need not be used in their pure form because less pure materials, which contain traces of growth factors and considerable quantities of mineral nutrients, are also suitable for use.

When desired, there may be added to the medium mineral salts such as calcium carbonate, sodium or potassium phosphate, sodium or potassium chloride, magnesium salts, copper salts and the like.

If necessary, especially when the culture medium foams seriously a defoaming agent, such as liquid paraffin, fatty oil, plant oil, mineral oil or silicone may be added.

As in the case of the preferred methods used for the production of other antibiotics in massive amounts, submerged aerobic cultural conditions are preferred for the production of WS 6049 substances in massive amounts.

For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the WS 6049 substances. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medium, in which the vegetative inoculum is produced, is substantially the same as or different from the medium utilized for the production of WS 6049 substances.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-30° C., for a period of about 50 hours to 100 hours.

When the fermentation is completed, the culture broth is then subjected for recovery of WS 6049 substances to various procedures conventionally used for recovery and purification of antibiotics, for instance, solvent extraction with an appropriate solvent or a mixture of such solvents, chromatography, or recrystallization from an appropriate solvent or a mixture of such solvent.

According to this invention, in general, WS 6049 substances are found mainly in the cultured mycelia. Accordingly, the culture broth is separated by means of filtration or centrifuging to provide the mycelium cake, and then WS 6049 substances are recovered from said resulting mycelium cake by means of extraction using an appropriate organic solvent such as acetone, ethyl acetate or the like, or a mixture of such solvents.

The extract is treated by a conventional manner to provide WS 6049 substances, for example, the extract is concentrated by evaporation or distillation to a smaller amount and the resulting residue containing active materials, i.e. WS 6049 substances are purified by conventional purification procedures, for example, chromatography or recrystallization from an appropriate solvent or a mixture of such solvents.

WS 6049-A substance and WS 6049-B substance can be separated by dissolving the materials containing both product produced by fermentation in an appropriate organic solvent such as chloroform or the like and then by chromatographing the solution, for example, on silica gel in a column with an appropriate organic solvent or a mixture of such solvents such as chloroform, acetone or the like and each of WS 6049-A substance and WS 6049-B substance thus separated can be further purified by a conventional method, for example, high performance liquid chromatography.

PHYSICAL AND CHEMICAL PROPERTIES OF WS 6049 SUBSTANCES

The WS 6049 substances i.e. WS 6049-A substance and WS 6049-B substance as obtained according to the aforementioned process have the following physical and chemical properties.

WS 6049-A (1) Form and color:
   Colorless powder.
(2) Color reaction:
   Positive: Dragendorff reaction, Ehrlich's reaction and cerium sulfate reaction.
   Negative: ninhydrin reaction.
(3) Solubility:
   Soluble: methanol, acetone, chloroform.
   Slightly soluble: diethyl ether.
   Insoluble: hexane, water.
(4) Melting point:

150° C. (dec.).

(5) Specific rotation:

$[\alpha]_D^{25} = -208°$ (c=1.0, CHCl$_3$).

(6) Ultraviolet absorption spectrum:

$$\lambda_{max}^{CH3OH} = 252 \text{ nm } (E_{1cm}^{1\%} = 560)$$
$$= 280 \text{ nm } (E_{1cm}^{1\%} = 370)$$
$$= 320 \text{ nm } (E_{1cm}^{1\%} = 220)$$

$\lambda_{max}^{CH3OH+HCl} = 252, 280, 320$ nm.
$\lambda_{max}^{CH3OH+NaOH} = 250, 280,$ ca310(sh.)nm.

(7) Infrared absorption spectrum:

$\nu_{max}^{CHCl3} = 3450, 3350, 3250, 2960, 2920, 1725, 1675, 1610, 1595, 1520, 1465, 1450, 1405, 1370, 1350, 1310, 1250, 1180, 1155, 1115, 1075, 1020, 985, 955, 905, 850$ cm$^{-1}$.

(8) Elementary analysis:

C: 52.03%, H: 5.71%, N: 4.15%, S: 9.86%.

(9) Thin layer chromatography:

| Stationary phase | Developing solvent | Rf value |
|---|---|---|
| Silica gel sheet | Chloroform: methanol (10:1)(v/v) | 0.59 |
|  | Chloroform: acetone (1:1)(v/v) | 0.33 |

(10) Molecular weight:

FD Mass: m/z 1333 (M$^+$+Na).
FABQ MS: m/z 1311 (M$^+$+1).
Gel permeation chromatography: 1100 to 1200.

(11) $^{13}$C Nuclear magnetic resonance spectrum (CDCl$_3$):

δ (ppm): 13.9, 14.6, 16.7, 17.6, 19.9, 22.8, 29.1, 34.0, 35.2, 39.6, 42.3, 52.7, 55.8, 56.1, 56.2, 56.2, 60.3, 61.7, 64.7, 66.7, 68.4, 69.0, 69.3, 69.8, 70.5, 72.0, 75.9, 76.1, 77.2, 77.3, 83.2, 86.3, 88.5, 90.7, 97.3, 98.6, 98.9, 99.6, 99.7, 103.9, 107.8, 112.7, 123.2, 125.0, 130.0, 131.1, 136.8, 144.2, 146.6, 154.0, 154.6, 160.9, 166.6, 192.4, as shown in FIG. 1 of the accompanying drawing.

(12) $^1$H Nuclear magnetic resonance spectrum (CDCl$_3$):

δ (ppm): 8.57 (1H, s), 7.48 (1H, s), 6.6 (1H,d,d), 6.2 (1H, d, J=1.6 Hz), 6.18 (1H, br.s.), 5.93 (1H, d, J=9.6 Hz), 5.83 (1H, d.d. J=9.6, 1.6 Hz), 5.7 (1H, d, J=2 Hz), 5.5 (1H, m), 5.48 (1H, d, J=2.3 Hz), 5.43 (1H, br.s), 4.97 (1H, d), 4.7 (2H, m), 4.56 (1H, d, J=2.3 Hz), 4.23 (1H, s), 4.2 to 3.6 (10 to 14H), 3.97 (3H, s), 3.88 (3H, s), 3.79 (3H, s), 3.5 (2H, m), 3.43 (3H, s), 2.77 (1H. s), 2.7 (2H, m), 2.52 (3H, s), 2.5 (1H, m), 2.4 to 2.25 (3H, m), 2.17 (1H, s), 2.12 (3H, s), 2.07 (1H, m), 1.77 (2H, s), 1.5 (2H, m), 1.41 (3H, d, J=6 Hz), 1.35 (3H, d, J=6 Hz), 1.32 (3H, d, J=6 Hz), 1.2 (4H, m), as shown in FIG. 2 of the accompanying drawing.

WS 6049-B (1) Form and color:
Colorless powder.

(2) Color reaction:
Positive: Dragendorff reaction, Ehrlich's reaction and cerium sulfate reaction.
Negative: ninhydrin reaction.

(3) Solubility:
Soluble: methanol, acetone, chloroform.
Slightly soluble: diethyl ether.
Insoluble: hexane.

(4) Melting point:
145° C. (dec.).

(5) Specific rotation:
$[\alpha]_D^{25} = -201°$ (c=1.0, CHCl$_3$).

(6) Ultraviolet absorption spectrum:

$$\lambda_{max}^{CH3OH} = 253 \text{ nm } (E_{1cm}^{1\%} = 620)$$
$$= 280 \text{ nm } (E_{1cm}^{1\%} = 450)$$
$$= 320 \text{ nm } (E_{1cm}^{1\%} = 250)$$

$\lambda_{max}^{CH3OH+HCl} = 253, 280, 320$ nm.
$\lambda_{max}^{CH3OH+NaOH} = 250, 282, 310$ (sh.) nm.

(7) Infrared absorption spectrum:

$\nu_{max}^{CHCl3} = 3450, 3350, 3250, 2990, 2920, 1725, 1675, 1610, 1595, 1520, 1465, 1450, 1405, 1370, 1350, 1310, 1250, 1180, 1155, 1115, 1070, 1020, 985, 955, 905, 880, 850$ cm$^{-1}$.

(8) Elementary analysis:
C: 51.58%, H: 5.75%, N: 4.27%, S: 9,80%.

(9) Thin layer chromatography:

| Stationary phase | Developing solvent | Rf value |
|---|---|---|
| Silica gel sheet | chloroform: methanol(10:1) (v/v) | 0.53 |
|  | chloroform: acetone(1:1) (v/v) | 0.18 |

(10) Molecular weight:
Gel permeation chromatography: 1100 to 1200.

(11) $^{13}$C Nuclear magnetic resonance spectrum (CDCl$_3$):

δ (ppm): 13.8, 16.7, 17.6, 19.8, 22.7, 29.1, 33.9, 34.1, 35.2, 39.5, 52.8, 55.8, 56.1, 56.3, 61.0, 61.5, 64.6, 66.7, 68.4, 69.0, 69.3, 69.8, 70.4, 71.9, 75.9, 76.2, 76.7, 77.2, 77.3, 77.6, 83.2, 86.6, 88.3, 90.7, 97.3, 98.6, 99.0, 99.6, 99.7, 103.9, 107.8, 112.7, 123.2, 124.9, 129.8, 131.0, 136.8, 144.2, 146.3, 154.0, 154.6, 160.9, 166.6, 192.4, as shown in FIG. 3 of the accompanying drawing.

(12) $^1$H Nuclear magnetic resonance spectrum (CDCl$_3$):

δ (ppm): 11.75 (1H, s), 8.57 (1H, s), 7.48 (1H, s), 6.6 (1H, d.d.), 6.24 (1H, d, J=1.3 Hz), 6.18 (1H, br.s), 5.93 (1H, d, J=9.2 Hz), 5.83 (1H, d.d, J=9 Hz and 1.3 Hz), 5.70 (1H, br.d), 5.5 (1H, m), 5.47 (1H, d, J=2.3 Hz), 5.42 (1H, br.s), 4.98 (1H, d, J=9 Hz), 4.70 to 4.6 (2H, m), 4.56 (1H, d, J=2.3 Hz), 4.24 (1H, s), 4.15 to 3.4 (12 to 18H), 3.97 (3H, s), 3.88 (3H, s), 3.79 (3H, s), 3.42 (3H, s), 2.52 (3H, s), 2.6 to 2.4 (2H, m), 2.4 to 2.2 (7 to 8H), 2.12 (3H, s), 2.2 to 2.0 (2H, m), 1.5 (2H, m), 1.4 (3H, d, J=6 Hz), 1.35 (3H, d, J=6 Hz), 1.33 (3H, d, J=6 Hz), as shown in FIG. 4 of the accompanying drawing.

BIOLOGICAL PROPERTIES OF WS 6049 SUBSTANCES

Biological properties of WS 6049 substances are explained in the following.

(1) Antitumor activities of WS 6049 substances:

The antitumor activities of WS 6049 substances were determined in experimental tumor system in mice.

Lymphocytic leukemia P-388 was implanted intraperitoneally into BDF$_1$ mice at an inoculum size of $1 \times 10^6$ cells per mouse. Twenty-four hours after the implantation of tumor cells, graded doses of the antibiotics were administered to mice intraperitoneally. Treatments were given on day 1, 2, 3 and 4.

The WS 6049 substances were suspended in physiological saline solution (0.9% saline). Control animals received intraperitoneal doses of physiological saline solution. The injection volume was 0.2 ml in all experiments.

The therapeutic responses measured was mean survival time, and results were expressed as T/C% (survival time of treated group/survival time of control group $\times$ 100). Toxicity was measured as weight loss between Days 0 and 4 after tumor inoculation.

The result is presented in Table 6 and Table 7. The WS 6049-A and WS 6049-B were quite active against the leukemia P-388. Doses between 0.025–12.0 μg/kg on the schedule resulted in significant increase in life span in mice.

TABLE 6

P-388 mouse leukemia
BDF$_1$ mouse (♀, 7 week)
tumor site i.p. (1 × 10$^6$ cells/mouse, day 0)
drug route i.p. (day 1,2,3 and 4)
five mice per group

| Drug | Dose (μg/kg/day) | Weight change (g) Day 0–Day 4 | Mean survival time (days) | T/C % |
|---|---|---|---|---|
| WS 6049-A | 25 · μg/kg/day | −3.1 | 7.6 | toxic |
| | 12 | −2.0 | 16.4 | 173 (1/5)* |
| | 6 | +0.1 | 21.5 | 226 |
| | 3 | +0.2 | 21.5 | 226 (1/5)* |
| | 1.5 | +0.2 | 22.5 | 237 |
| | 0.8 | +0.3 | 22.0 | 232 |
| | 0.4 | +0.2 | 21.6 | 227 |
| | 0.2 | +0.2 | 20.0 | 211 |
| | 0.1 | +0.2 | 18.6 | 196 |
| | 0.05 | +0.1 | 16.6 | 175 |
| | 0.025 | +0.6 | 12.3 | 129 |
| Control | — | +1.0 | 9.5 | 100 |

*Numbers of survivor at Day 30 / Total mice

TABLE 7

P-388 mouse leukemia
BDF$_1$ mouse (♀, 7 week)
tumor site i.p. (1 × 10$^6$)
drug route i.p. (day 1,2,3 & 4)
five mice per group

| Drug | Dose | Weight change (g) Day 0–Day 4 | Mean survival time (days) | T/C % |
|---|---|---|---|---|
| WS 6049-B | 10 μg/kg/day | −1.7 | 8.9 | 72 |
| | 3.3 | −0.4 | 26.4 | 215 |
| | 1.1 | −1.2 | 20.7 | 168 |
| | 0.37 | +0.3 | 23.3 | 189 |
| | 0.12 | 0 | 21.9 | 178 |
| | 0.04 | +0.5 | 24.8 | 202 |
| | 0.013 | +0.6 | 17.7 | 144 |
| Control | vehicle 0.2 ml/ mouse/day | +0.6 | 12.3 | 100 |

(2) Antimicrobial activities of WS 6049-A and WS 6049-B

The antimicrobial activities of WS 6049-A and WS 6049-B were determined by a serial broth dilution method in bouillon medium for bacteria and in Sabouraud medium for fungi and yeast. Minimum inhabitory concentrations (MIC) were expressed in terms of μg/ml after overnight incubation at 37° C. for bacteria and 48–72 hours incubation at 28° C. for fungi and yeasts. The antimicrobial spectra of WS 6049-A and WS 6049-B are shown in Table 8.

From the results, the antibiotics, WS 6049 substances have a broad antimicrobial activity and may be among the most potent antibiotics ever discovered.

TABLE 8

Antimicrobial spectra of WS 6049-A and WS 6049-B

| | MIC (μg/ml) | |
|---|---|---|
| Microorganism | WS 6049-A | WS 6049-B |
| Staphylococcus aureus 209 P | 0.0001–0.0002 | 0.0001–0.0002 |
| Bacillus subtilis | 0.001 | 0.001 |
| Escherichia coli | 0.6 | 0.6 |
| Pseudomonas aeruginosa | 0.6 | 0.6 |
| Proteus vulgaris | 1.2 | 1.2 |
| Candida albicans | 5.0 | 5.0 |
| Aspergillus oryzae | 0.6 | 0.6 |
| Penicillium chrysogenum | 0.3 | 0.3 |
| Aureobasidium sp. | 0.15 | 0.15 |

(3) Acute toxicity of WS 6049-A and WS 6049-B

Acute toxicity of WS 6049-A and B in ddY mice by intraperitoneal injection are both 0.05 mg/kg.

The pharmaceutical composition of this invention can be used in the form of a pharmaceutical preparation, for example, in solid, semisolid or liquid form, which contains WS 6049 substances, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, or suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition further comprise auxiliary, stabilizing, thickening and coloring agents and perfumes may be used. The active object compound is included in the pharmaceutical composition in an amount sufficient to produce the desired antimicrobial effect upon the process or condition of diseases.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily dose of about 0.01–50 μg of the active ingredient/kg of a human being or an animal is generally given for treating diseases, and an average single dose of about 0.1 μg, 1 μg, 10 μg, 50 μg, 100 μg and 200 μg is generally administered.

The following examples are given for the purpose of illustrating the present invention.

EXAMPLES

Example 1

An aqueous medium (160 ml) containing 2% starch, 0.5% glucose, 1% cotton seed flour, 1% dried yeast, 0.5% corn steep liquor and 0.2% CaCO$_3$ (pH 7.0) was poured into each of three 500 ml Erlenmeyer flasks and sterilized at 120° C. for 30 minutes. A loopful of slant culture of *Actinomadura pulveraceous* sp. nov. No. 6049 (ATCC 39100) was inoculated to each of the medium and cultured at 30° C. on a rotary shaker with 3-inch throw at 220 rpm for 4 days. The resultant culture was inoculated to an aqueous medium (20 liters) containing 4% sucrose, 0.5% dried yeast, 0.1% $K_2HPO_4$, 0.1% $MgSO_4.7H_2O$, 0.1% NaCl, 0.2% $(NH_4)_2SO_4$, 0.2% $CaCO_3$, 0.0001% $FeSO_4.7H_2O$, 0.0001% $MnCl_2.4H_2O$, 0.0001% $ZnSO_4.7H_2O$ and 0.00005% of NaI in a 30 liter jar-fermentor, which had been sterilized at 120° C. for 30 minutes, and cultured at 30° C. for 4 days under aeration of 20 liters/minute and agitation of 300 r.p.m.

The cultured broth thus obtained was filtered with an aid of diatomaseous earth (1 kg). To the mycelia obtained were added 10 liters of ethyl acetate and stirred for 10 minutes. This extraction procedure was carried out twice and the extracts were combined. The extracts were washed with 10 liters of 1% sodium bicarbonate and 10 liters of 10% sodium chloride. Then the extracts were concentrated in vacuo to a volume of one liter. After dehydration with anhydrous sodium sulfate, the ethyl acetate solution was further concentrated in vacuo and the oily materials obtained were applied to a column chromatography using silica gel (70 ml). The column was washed with 200 ml of chloroform and eluted with a mixture of chloroformmethanol (40:1). Fractions containing active materials (500 ml) were concentrated in vacuo to give a crude powder (140 mg).

The powder was dissolved into 2 ml of chloroform and subjected to a column of silica gel (20 ml). The column was washed with a mixture of chloroform-acetone (8:1), and WS 6049-A was eluted with a mixture of chloroform-acetone (4:1). WS 6049-B was eluted with a mixture of chloroform-acetone (2:1).

Each of fractions containing WS 6049-A and WS 6049-B was concentrated in vacuo to give a crude powder of WS 6049-A (17 mg) and WS 6049-B (15 mg), respectively. They were separately subjected to high performance liquid chromatography (HPLC). HPLC was carried out using a Waters Model 6000 A pump with a Waters Model U6K injector. Chromatography was monitored by a UV detector, Waters Model 440 at 254 nm. A steel column (7.9 mm inside diameter, 300 mm length) packed with a μ Porasil (Merck, Darmstadt) was used at a flow rate of 3 ml/minutes. Mobile phase used was a mixture of hexane, chloroform and methanol (25:10:2). HPLC under the above-mentioned conditions gave fraction A (retention time: 18 min.) and fraction B (retention time: 26 min.). Twelve mg of colorless powder of WS 6049-A from fraction A and 8 mg of colorless powder of WS 6049-B from fraction B were obtained.

We claim:

1. A WS 6049 substance selected from the group consisting of WS 6049-A substance and WS 6049-B substance, wherein (i) the WS 6049-A substance has the following properties:

(1) Form and color: Colorless powder (2) Color reaction:
Positive: in Dragendorff reaction, Ehrlich's reaction and cerium sulfate reaction
Negative: in ninhydrin reaction (3) Solubility
Soluble: in methanol, acetone, chloroform
Slightly soluble: diethyl ether
Insoluble: in hexane, water (4) Melting point: 150° C. (dec.)

(5) Specific rotation: $[\alpha]_D^{25} = -208°$ (C=1.0, $CHCl_3$)

(6) Ultraviolet absorption spectrum:

$\lambda_{max}^{CH3OH}$ = 252 nm ($E_{1cm}^{1\%}$ = 560)

= 280 nm ($E_{1cm}^{1\%}$ = 370)

= 320 nm ($E_{1cm}^{1\%}$ = 220)

$\lambda_{max}^{CH3OH+HCl}$ = 252, 280, 320 nm
$\lambda_{max}^{CH3OH+NaOH}$ = 250, 280, ca310 (sh.)nm (7) Infrared absorption spectrum:
$\nu_{max}^{CHCl3}$ = 3450, 3350, 3250, 2960, 2920, 1725, 1675, 1610, 1595, 1520, 1465, 1450, 1405, 1370, 1350, 1310, 1250, 1180, 1155, 1115, 1075, 1020, 985, 955, 905, 805 $cm^{-1}$ (8) Elementary analysis:
C: 52.03%, H: 5.71%, N: 4.15%, S: 9.86%

(9) Thin layer chromatography:

| Stationary Phase | Developing Solvent | Rf value |
|---|---|---|
| Silica gel sheet | chloroform: methanol (10:1)(v/v) | 0.59 |
|  | chloroform: acetone (1:1)(v/v) | 0.33 |

(10) Molecular weight:
FD Mass: m/z 1333 ($M^+ + Na$)
FABQ MS: m/z 1311 ($M^+ + 1$)
Gel permeation chromatography: 1100–1200

(11) $^{13}C$ Nuclear magnetic resonance spectrum ($CDCl_3$):

δ (ppm): 13.9, 14.6, 16.7, 17.6, 19.9, 22.8, 29.1, 34.0, 35.2, 39.6, 42.3, 55.8, 56.1, 56.2, 56.2, 60.3, 61.7, 68.4, 69.0, 69.3, 69.8, 70.5, 72.0, 75.9, 76.1, 77.2, 77.3, 83.2, 86.3, 88.5, 90.7, 97.3, 98.6, 98.9, 99.6, 99.7, 103.9, 107.8, 112.7, 123.2, 125.0, 130.0, 131.1, 136.8, 144.2, 146.6, 154.0, 154.6, 160.9, 166.6, 192.4, as shown in FIG. 1 of the accompanying drawing, (12) $^1H$ Nuclear magnetic resonance spectrum ($CDCl_3$):

δ (ppm): 8.57 (1H, s), 7,.48 (1H, s), 6.6 (1H, d.d), 6.2 (1H, d, J=1.6 Hz), 618 (1H, br.s), 5.93 (1H, d, J=9.6 Hz), 5.83 (1H, d.d J=9.6, 1.6 Hz), 5.7 (1H, d, J=2 Hz), 5.5 (1H, m), 5.48 (1H, d, J=2.3 Hz), 5.43 (1H, br.s), 4.97 (1H, d), 4.7 (2H, m), 4.56 (1H, d, J=2.3 Hz), 4.23 (1H, s), 4.2 to 3.6 (10 to 14H), 3.97 (3H, s), 3.88 (3H, s), 3.79 (3H, s), 3.5 (2H, m), 3.43 (3H, s), 2.77 (1H, s), 2.7 (2H, m), 2.52 (3H, s), 2.5 (1H, m), 2.4 to 2.25 (3H, m), 2.17 (1H, s), 2.12 (3H, s), 2.07 (1H, m), 1.77 (2H, s), 1.5 (2H, m), 1.41 (3H, d, J=6 Hz), 1.35 (3H, d, J=6 Hz), 1.32 (3H, d, J=6 Hz), 1.2 (4H, m), as shown in FIG. 2 of the accompanying drawing, and (ii) the WS 6049-B substance has the following properties:

(1) Form and color: Colorless powder (2) Color reaction:
Positive: in Dragendorff reaction, Ehrlich's reaction and cerium sulfate reaction
Negative: in ninhydrin reaction (3) Solubility:

Soluble: in methanol, acetone, chloroform
Slightly soluble: in diethyl ether
Insoluble: in hexane (4) Melting point: 145° C. (dec.), (5) Specific rotation: $[\alpha]_D^{25} = -201 \cup (c=1.0, CHCl_3)$ (6) Ultraviolet absorption spectrum:

$$\lambda_{max}^{CH3OH} = 253 \text{ nm } (E_{1cm}^{1\%} = 620)$$
$$= 280 \text{ nm } (E_{1cm}^{1\%} = 450)$$
$$= 320 \text{ nm } (E_{1cm}^{1\%} = 250)$$

$\lambda_{max}^{CH3OH+HCl} = 253, 280, 320$ nm
$\lambda_{max}^{CH3OH+NaOH} = 250, 282, 310$ (sh.) nm (7) Infrared absorption spectrum:
$\nu_{max}^{CHCl3} = 3450, 3350, 2990, 2920, 1725, 1675, 1610, 1595, 1520, 1465, 1450, 1405, 1370, 1350, 1310, 1250, 1180, 1155, 1115, 1070, 1020, 985, 955, 905, 880, 850$ cm$^{-1}$ (8) Elementary analysis:
C: 51.58%, H: 5.75%, N: 4.27%, S: 9.80%

(9) Thin layer chromatography:

| Stationary Phase | Developing Solvent | Rf value |
|---|---|---|
| Silica gel sheet | chloroform: methanol (10:1)(v/v) | 0.53 |
|  | chloroform: acetone (1:1)(v/v) | 0.18 |

(10) Molecular weight: 1100 to 1200 by
Gel permeation chromatography [:1100 to 1200]

(11) $^{13}$C Nuclear magnetic resonance spectrum (CDCl$_3$):

δ (ppm): 13.8, 16.7, 17.6, 19.8, 22.7, 29.1, 33.9, 34.1, 35.2, 39.5, 52.8, 55.8, 56.1, 56.3, 61.0, 61.5, 64.6, 66.7, 68.4, 69.0, 69.3, 69.8, 70.4, 71.9, 75.9, 76.2, 76.7, 77.2, 77.3, 77.6, 83.2, 86.6, 88.3, 90.7, 97.3, 98.6, 99.0, 99.6, 99.7, 103.9, 107.8, 112.7, 123.2, 124.9, 129.8, 131.0, 136.8, 144.2, 146.3, 154.0, 154.6, 160.9, 166.6, 192.4, as shown in FIG. 3 of the accompanying drawing, (12) H Nuclear magnetic resonance spectrum (CDCl$_3$):

δ (ppm): 11.75 (1H, s), 8.57 (1H, s), 7.48 (1H, s), 6.6 (1H, d.d.), 6.24 (1H, d, J=1.3 Hz), 6.18 (1H, br.s), 5.93 (1H, d, J=9.2 Hz), 5.83 (1H, d.d, J=9 Hz and 1.3 Hz), 5.70 (1H, br.d), 5.5 (1H, m), 5.47 (1H, d, J=2.3 Hz), 5.42 (1H, br.s), 4.98 (1H, d, J=9 Hz), 4.7 to 4.6 (2H, m), 4.56 (1H, d, J=2.3 Hz), 4.24 (1H, s), 4.15 to 3.4 (12 to 18H), 3.97 (3H, s), 3.88 (3H, s), 3.79 (3H, s), 3.42 (3H, s), 2.52 (3H, s), 2.6 to 2.4 (2H, m), 2.4 to 2.2 (7 to 8H), 2.12 (3H, s), 2.2 to 2.0 (2H, m), 1.5 (2H, m), 1.4 (3H, d, J=6 Hz), 1.35 (3H, d, J=6 Hz), 1.33 (3H, d, J=6 Hz), as shown in FIG. 4 of the accompanying drawing.

2. An antimicrobial composition comprising:
(a) the substance WS 6049-A or 6049-B of claim 1 in an amount between about 0.1 and 200 μg., and
(b) a pharmaceutically acceptable carrier.

3. The WS 6049 substance of claim 1 wherein the WS 6049 substance is WS 6049-A.

4. The WS 6049 substance of claim 1 wherein the WS 6049 substance is WS 6049-B.

5. The composition in claim 2 in the form of tablets, pellets, capsules, suppositories, solutions, emulsions, or suspensions.

6. The composition of claim 2 for external, enteral or parenteral application.

7. The composition of claim 2 wherein the carrier is selected from the group consisting of water, glucose, lactose, gum acacia, gelatin, mannitol, starch paste, magnesium trisilicate, talc, corn starch, keratin, colloidal silica, potato starch, and urea.

8. The composition of claim 2 further comprising an agent selected from the group consisting of stabilizing, thickening and coloring agents and perfumes.

* * * * *